US007656402B2

(12) United States Patent
Abraham et al.

(10) Patent No.: US 7,656,402 B2
(45) Date of Patent: Feb. 2, 2010

(54) METHOD FOR CREATING, MANUFACTURING, AND DISTRIBUTING THREE-DIMENSIONAL MODELS

(75) Inventors: Thomas G. Abraham, Miami, FL (US); Henry Gonzalez, Miami Springs, FL (US)

(73) Assignee: TAHG, LLC, Coral Gables, FL (US)

( * ) Notice: Subject to any disclaimer, the term of this patent is extended or adjusted under 35 U.S.C. 154(b) by 0 days.

(21) Appl. No.: 11/873,679

(22) Filed: Oct. 17, 2007

(65) Prior Publication Data

US 2008/0111816 A1 May 15, 2008

Related U.S. Application Data

(60) Provisional application No. 60/865,852, filed on Nov. 15, 2006.

(51) Int. Cl.
*G06T 17/00* (2006.01)
(52) U.S. Cl. .................. 345/420; 345/419; 345/473; 345/541; 382/85; 382/100; 705/1; 705/2; 705/26
(58) Field of Classification Search ............... 345/419, 345/420, 473, 541; 352/85; 382/85, 100; 705/1, 2, 26
See application file for complete search history.

(56) References Cited

U.S. PATENT DOCUMENTS 6,549,639 B1 * 4/2003 Genest ................. 382/100

| 6,725,124 | B2 | 4/2004 | Yan |
| 6,912,293 | B1 * | 6/2005 | Korobkin ............ 382/100 |
| 7,065,242 | B2 | 6/2006 | Petrov et al. |
| 7,392,559 | B2 * | 7/2008 | Peterson .............. 12/1 R |
| 2002/0156652 | A1 | 10/2002 | Sachdeva et al. |
| 2003/0033207 | A1 * | 2/2003 | Litke et al. ............ 705/26 |
| 2003/0132966 | A1 | 7/2003 | Simas et al. |
| 2003/0160970 | A1 | 8/2003 | Basu et al. |
| 2004/0073446 | A1 | 4/2004 | Snow |

(Continued)

OTHER PUBLICATIONS

Toy Builders.com-"Largest Custom Toymaker in the World" (also uses 3D Technology), http://www.toybuilders.com/index.html.

(Continued)

*Primary Examiner*—Kimbinh T Nguyen
(74) *Attorney, Agent, or Firm*—Feldman Gale PA; Rafael A. Perez-Pineiro; Michael C. Cesarano

(57) ABSTRACT

A method is provided for producing three-dimensional (3D) models. The invention will take any sculpture, character, or model from artwork, still life models, images of human beings, characters from a computer game, or any other 3D digital image or model that is scanned, and turn the digital image into 3D models. The method is comprised of the following steps: creating a user account in a computer storage area; storing 3D images under the user account; allowing the user to select the 3D image(s) he or she wants to create as 3D models; manufacturing the 3D models; and delivering the models to the user or to a specified third-party. An online storefront and/or auction system may allow each user the opportunity to sell their 3D models or purchase other users' 3D models. The system may also create 3D models for a mobile phone and portable media player while transferring the models to either of these devices.

11 Claims, 5 Drawing Sheets

U.S. PATENT DOCUMENTS

| | | | |
|---|---|---|---|
| 2004/0257361 A1* | 12/2004 | Tabakman et al. | 345/419 |
| 2005/0010450 A1 | 1/2005 | Hultgren et al. | |
| 2005/0190962 A1 | 9/2005 | Liu et al. | |
| 2005/0234860 A1* | 10/2005 | Roever et al. | 707/1 |
| 2006/0104503 A1* | 5/2006 | Huang et al. | 382/154 |
| 2006/0129461 A1 | 6/2006 | Pankl et al. | |
| 2007/0043630 A1 | 2/2007 | Lyden | |

OTHER PUBLICATIONS

Davison Inventegration-"We build your idea into a product sample and present it to corporations.", http://www.davison54.com/.

3D Proto, Inc.-"allow[s] engineers, designers, and architects to make prototype models a common part of their design process and minimize the time to market", http://www.3dproto.com/html_1/index.php.

* cited by examiner

200

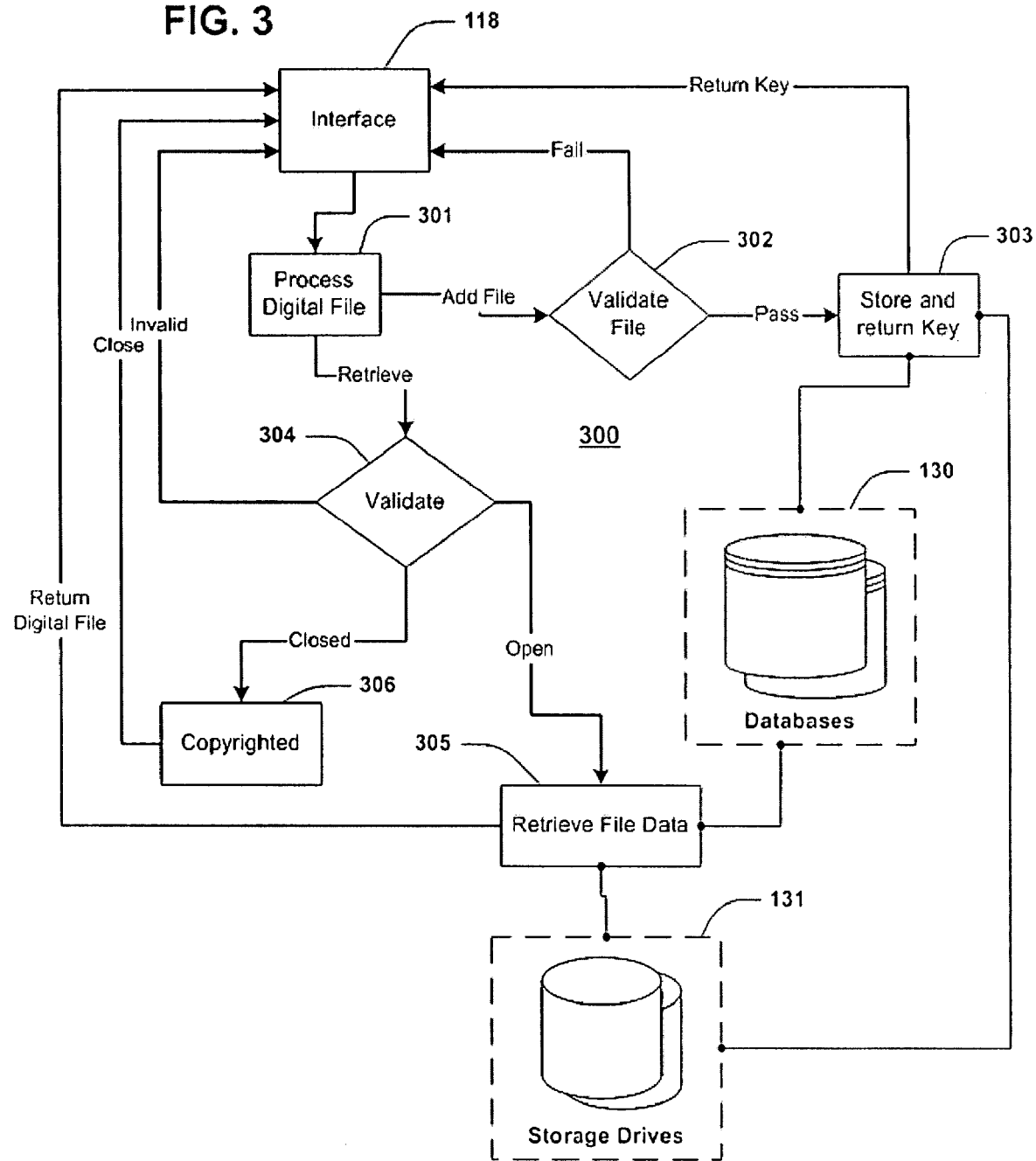

METHOD FOR CREATING, MANUFACTURING, AND DISTRIBUTING THREE-DIMENSIONAL MODELS

CROSS-REFERENCE TO RELATED APPLICATIONS

This application claims the priority benefit of U.S. Provisional Application No. 60/865,852 filed Nov. 15, 2006, now pending, which is incorporated herein by reference.

FIELD OF THE INVENTION

This invention relates to the field of computer aided manufacturing and selling of 3D models via a remotely accessible network or retail storefront.

BACKGROUND OF THE INVENTION

There are several methods currently available for creating a 3D computer model of an object. For instance, U.S. Pat. No. 7,079,114 B1 teaches an interactive method for designing automobiles that aids in creating a 3D computer model. Also, U.S. Publication No. 2006/0232583 A1 teaches a method for capturing a physical model as a 3D computer model. Other systems are available for creating a 3D model from a 2D image. For example, U.S. Publication No. 2005/0190962 A1 demonstrates a method for creating a 3D computer model of a face from standard, two-dimensional (2D) images. However, the above references share the same general modelive of creating a 3D image inside a computer system, instead of providing a user-friendly system for producing a tangible, 3D model or reproduction, or producing other 3D models.

Some inventions have recognized the usefulness of creating a physical reproduction of a 3D computer model. For example, U.S. Publication No. 2004/0243481 discloses the creation of a 3D computer model based on a medical patient's physical characteristics, along with transmission of the model over the internet so that it may be manufactured into a physical manifestation of the 3D model for use in medical procedures.

Several inventions also exist for the creation of 3D animations related to video games, and have recognized the potential value of being able to buy and sell such creations. For example U.S. Publication No. 2004/0053690 A1 pertains to customizing digital, 3D characters and then buying and selling them over the internet.

However, no invention currently exists for a secured network-based system designed for use over the internet, in a retail store, or third-party location, which allows users with no experience in creating 3D models to have 3D models manufactured from their 3D images, and to collect, buy, sell, and ship the models while optionally employing an automated system to register the models for copyright protection. Also, none of the above-cited inventions allows computer aided production of animated film clips, video games, and mobile phone models incorporating the user's 3D images, nor do they allow the certification of the 3D models so that it may be bought and sold as unique models.

SUMMARY OF INVENTION

The novel invention described below defines a convenient, user-friendly solution for the creation of 3D models so that a user with no prior experience with 3D imaging or manufacturing can easily create 3D models in various formats, and receive a certificate of authenticity for their 3D models, either from their personal computer over the internet or by visiting a retail store or third-party vendor location. Also, if the user desires, the user may elect to have their 3D models sold in an auction, or to purchase other users' 3D models through the use of the same auction system.

A user interacts with the invention through a remotely-accessible user interface via the internet or at a retail or third-party location. The user may upload digital images and convert 2D images into 3D images, upload a digital image of a customizable video game and/or virtual world character, or scan a person or other model using a 3D scanner. Then, the user may select which 3D images the user wishes to have manufactured into various forms of 3D models. The invention will manufacture the 3D models from the user's digital image in accordance with the user's specifications, and may optionally automatically register the unique 3D models for copyright protection. After the quality and accuracy of the 3D models is assured, it is shipped to the location the user has specified. Additionally, a user may elect to have their 3D images incorporated into an animated film or video game by selecting from available storyboards and/or video game templates, or may have their 3D models incorporated into various mobile phone and/or portable media player usable formats and sent to their mobile phone and/or portable media player either by a direct link or over a wireless network.

If the user desires, the user may place his or her 3D models for sale in an online auction, or the user may purchase 3D models from other users. Upon the sale of their models, the selling user will no longer have access to the 3D image, and the purchasing user will be granted access and will be issued a certificate of authenticity to certify that the model is unique. In order to ensure uniqueness of the 3D models, the invention may prevent a user from saving, copying, or modifying a 3D image once it has been manufactured, and may also prevent the user from ordering further copies of the models to be manufactured. If the 3D image has not been manufactured, then the invention may restrict the user to modify any part of the image.

BRIEF DESCRIPTION OF THE DRAWINGS

The invention is illustrated by way of example, and not by way of limitation in the figures of the accompanying drawings, in which:

FIG. 3 is a flow diagram of one embodiment of a Digital Lock Box system.

DETAILED DESCRIPTION OF THE INVENTION

Figure 1:
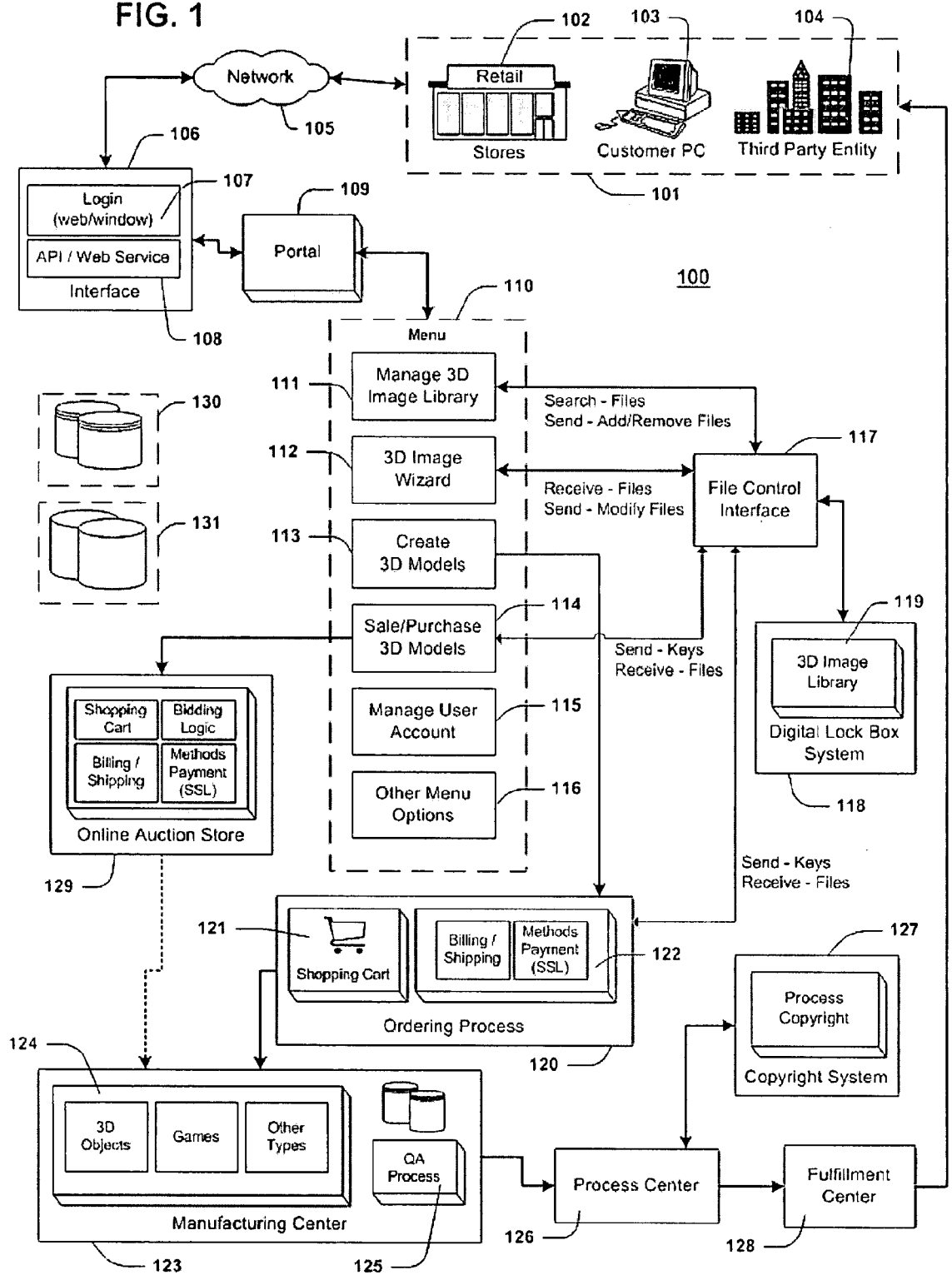
FIG. 1 is a flow diagram of one embodiment of the system in which the different embodiments of the present invention may operate.

FIG. 1 shows a diagram of the system 100 processes in accordance with the invention. In an embodiment, the system 100 could interface with multiple users 101 through one of the following means: a retail store 102; a customer home PC 103; or a third-party entity 104.

The interface 106 to the system 100 will be accessible over a wide-area network (WAN) 105, such as the Internet, extranet, LAN, or satellite communications. The World Wide Web environment also known as "the Web" could be used to exchange data or transact business. Users can connect via a personal or network computer, workstation, or minicomputer, using any operating system that is running any version of Windows, Windows NT, Window Server OS, MacOS, or any equivalent thereof. The invention may be implemented using several types of communication protocols, including but not limited to the following: TCP/IP; Appletalk; NetBIOS; OSI; or any future protocols. Data connections, such as Internet Service Providers (ISPs), cable modems, ISDN, Dish Networks, Digital Subscriber Line (DSL), and various wireless communication methods or any future communication methods, could serve as links to the WAN 105.

The communication medium between the system 100 and the various users 101 could be a direct link via a network interface 105 or via the Internet 105 using a commercially available Java-enabled and Javascript-enabled browser, such as the following: Internet Explorer™ from Microsoft Corporation; Mozilla; Safari; FireFox; Netscape from Netscape Navigator™; or similar browsers. The user connection to the system 100 could use a mechanism like Secure Socket Layer (SSL) and/or a firewall system to protect server data and algorithms from unauthorized access by intruders.

The system 100 architecture could use an N-tier and/or service oriented approach, implemented in a multi-platform (platform independent) format using any high-level programming language, such as the following: VB.NET/ASP.NET by Microsoft Corporation; C++; or Java. Other programming languages that may be used include but are not limited to the following: structured query language (SQL); hypertext markup language (HTML); scripting languages (i.e. VBScript, Javascript, etc.); Flash programming language; common gateway interface/structured query language (CGI/SQL); or any equivalent thereof. Information stored by the system 100 may be stored in a computerized database 130, such as a relational, hierarchical, an model-oriented database, or any equivalent thereof. Several commercially-available databases 130 may be used to implement the system, including any of the database products available from Microsoft Corporation, Oracle Corporation, DB2, Sybase, Mysequel, or any equivalent thereof. The system 100 storage devices 131 (e.g. optical discs, magnetic storage-like hard disks) could be implemented using any one of the following storage architectures: direct attached storage (DAS); network attached storage (NAS); storage area network (SAN); or any equivalent thereof. All the web pages may have active content using Java applets or ActiveX controls, or any other active content technology developed now or in the future. Also, the system 100 is not limited to the type of documents and applications that might be used to interact with the user, such as the following: active server pages (ASP); dynamic HTML; cascading style sheets (CSS); plug-ins; or any equivalent thereof.

The interface 106 is the gateway or entry point to the system 100. Users will have several ways to enter the system 100. Users could either log in through a web page 107 or via an application interface or web service 108. The log-in web pages 107 will have markup language-based information, such as hypertext markup language (HTML), or extensible markup language (XML). The log-in web page 107 may request the user to enter their log-in information. The user's identity may be authenticated via a password and a personal identification number (PIN). If the user is not a member of the system 100, a subscription-based membership and registration web page may load allowing the user to register to become a member.

In the registration form, the user must agree to assign the right to his or her image with respect to all aspects of the production of a sculpture and/or recreation of their image. When the user completes the subscription-based membership and registration, the system administrator and the new user will receive notification of membership. The new user membership information will be stored in several databases 130 and the new user's personal, portal 109 will be created. Once the user's membership information is registered in the system 100, the user is directed back to the log-in web page 107. Here, the user must supply their new log-in information to enter the system. If a user enters invalid log-in information, the system 100 may alert them of the error. Users who are validly logged in will be taken directly to their personal portal 109.

In another embodiment of the invention, the user may connect through a third-party entity 104 (e.g. retail business, partnerships, corporations, companies, non-profit organizations, etc.). The interface 106 could use web services 108 in conjunction with extensible mockup language (XML), simple object access protocol (SOAP), and/or any equivalent thereof, which provide a medium for companies to communicate via their servers to the system 100. Here, the user does not interact with the system 100 directly, but rather, via the third-party entity's 104 online retail website. A third-party entity 104 may embed the system 100 inside their web site while still providing the user the option to manage models and images. By making the system 100 a part of the third-party's website, the third-party entity 104 could eliminate the need to add special features to their own site to accommodate the users. Additionally, the system 100 may be customized to blend in with a third-party's web site theme.

The portal 109 is the core navigation menu system 110 which provides the user with numerous options, including but not limited to the following: managing personalized 3D digital image files 111; the 3D image wizard 112 which allows the user to alter and/or create new 3D images from a user's existing 3D image library 119; ordering 3D models 113 to be manufactured; using the online auction system 114 for sale or purchase of 3D models; and/or managing a membership account 115. A third-party entity that is interfacing with the system 100 may limit the menu options available to users on their web site.

The ability to manage 3D image files 111 is another aspect of this invention. Users can manage their own 3D image library 119 via the file control interface 117 of the digital lock box system 118. They can group their 3D images by category (key words defined by the user), by image file name, by image file date, by available images that have not yet been manufactured, and by images that have already been manufactured. Users can add new 3D images to their library 119 by uploading valid image files that meet the file format requirements of the system 100 (e.g. STL, PLY, VRML). The images are then stored in the user's private account in the digital lock box system 118. Also, users may remove 3D images that have not yet been manufactured into 3D models, but may not remove 3D images that have been manufactured into 3D models already.

A third-party entity 104 interfacing with the system 100 has the option to transfer specific 3D images that the customer selects on the third-party web site. Before transferring any images to the system 100, a user must first have an account. For new customers, the third-party entity 104 must transmit the customers' membership information via the API/web service interface 108 for registration in the system 100. Once the membership information is available, the third-party entity 104 will use this information to interface 106, 108 with the system 100. Then, the selected images on the third-party web site may be placed into the user's system digital lock box 118 user account. A "push" technology over some kind of secure wide-area network (WAN) used by the third-party entity 104 may be implemented to send the 3D images to the system 100 servers. Other technologies, such as web or window services 108 may also be implemented. The process will upload the files automatically to the digital lock box system 118 while updating the user's image library information in the database. The images may then be viewed in the user's 3D image library 119.

In another embodiment of the invention, there is a 3D Image Wizard 112 containing software that allows a user to modify or enhance an existing 3D image's geometry and texture information into a new 3D image file which is then stored back into the user's digital lock box 118 account. This feature 112 (i.e. similar to a paint brush concept to edit graphic digital files) may allow the users to create an assortment of other 3D models. Rendering software may be accessed by a user through the system to allow the user to convert a 2D image into a 3D image. The wizard 112 will allow users to add realistic or aesthetic depth to a 3D image through a process known as "texture mapping," "mapping," or "applying." A texture map is represented by a bitmap or other picture file formats such as JPEG, GIF, or TIFF. For example, the artwork of a painter may be scanned or photographed to a bitmap and then mapped onto a 3D image like a sculpture. This mapping can be accomplished through the use of any available software tool, such as the following: 3D Max Studio, Autodesk, Maya, Cinema 4D, or any equivalent thereof.

A user may create 3D models 113 using available 3D images in their digital lock box that have yet to be manufactured via the ordering process 120. As illustrated, the ordering process 120 contains components that are commonly found in a web commerce server including but not limited to the following: a shopping cart 121; billing/shipping order web pages; and/or method of payment 122 components. The process that facilitates electronic commerce is also known as "E-commerce," "e-business," or "I-commerce." The web commerce server may use various known encryption techniques (e.g. Advanced Encryption Standard [AES], Data Encryption Standard [DES], etc.), as well as secure socket layer (SSL) 122 to provide security to the users while placing their orders inside the system 100. Inside the shopping cart engine 121, the user may add 3D images from the user's private library 119 via the file control interface 117 by sending over the available file keys to the digital lock box system 118. Also, the user has the option to remove any 3D images from the shopping cart 121 before submitting the order to the manufacturing center 123. While the user is populating the shopping cart 121, the user has the option to choose the 3D model type for the 3D image, including but not limited to the following: creating 3D objects (e.g. 3D doll, sculpture, action figure, virtual environment action figure game components, 3D figures for board games like "Chess" pieces, other 3D retail figures); creating 3D video games (i.e. group of 3D images of little league baseball players to produce a baseball video game); creating 3D animation film (i.e. single or group of 3D images with audio files to produce an animation film based on a story); creating 3D mobile phone or portable media player products, and/or any equivalent thereof.

When the user is ready to manufacture the selected 3D model, the user clicks on the "Check-Out" button inside the shopping cart 121, and secure web pages 122 are then loaded with default billing and shipping information from the user's member account. Also, the user selects which shipping carrier (e.g. Federal Express, UPS) they want to use for their order. The user can alter the billing and shipping information if desired, and then the user proceeds to choose the method of payment 122 for the order. The system 100 may include, but is not limited to the following methods of payment 122: credit card; electronic check; debit card; bank deposit; or escrow. When the user is done filling out the method of payment 122, the payment is processed trough any of several commercially-available, payment-gateway services (e.g. Authorize.Net, Paymentonline, PayPal) via an application programming interface (API), HTTPS Post, or any equivalent thereof. When the payment gateway service returns a successful transaction status, then the purchase order is sent to and received by the manufacturing center 123. If a fail status is returned, the user may either enter another method of payment, or contact the support team. The purchase order consists of meta-data that describes the properties and attributes of the order, including but not limited to the following: user name; billing and shipping address; 3D image attributes; and any other unique identifiers used to retrieve additional information needed to create the 3D models. The 3D image file is simultaneously transmitted to and received by the manufacturing center 123 with the purchase order information. Any e-commerce components shown in the system 100 are for illustrative purposes and not meant as limitations to the implementation of the system. Other components may be used in addition to or in place of the illustrated components for providing a secure web commerce server.

Before the manufacturing center 123 produces the 3D models, a quality assurance (QA) 125 order process is performed by the manufacturing technicians to ensure the purchase order has all the 3D image attributes and any other additional information needed to create the 3D models. This process may eliminate mistakes in producing the wrong models for the user. Also, if something is wrong or missing, the order is placed on "Hold" until further information is provided to the manufacturing center 123. When the manufacturing center 123 is ready to proceed in producing the 3D models, the manufacturing technicians use the correct fabrication machinery, 2D/3D game development system, and/or digital content editing systems to produce the 3D models.

In one embodiment, the user is provided with the option to create a 3D object using their digital image files. The 3D objects can be manufactured utilizing a variety of fabrication means. Some examples of fabrication machinery 124 that can be used include, but are not limited to the following: 3D printers (e.g. any 3D printers from Z Corporation of Burlington, Mass. or any 3D printers from Dimension of Eden Prairie, Minn.); carving machinery; computer controlled milling machinery; plastic machinery; printing machinery; laser cutting machinery; water jet machinery; swing machinery; embroidery machinery; and/or any equivalent thereof. Many of these machines use software systems (i.e. computer-aided manufacturing system (CAM)) to assist while producing the models. For example, 3D printers input 3D image data files in several formats, including but not limited to the following: STL; VRML; PLY; any type of software that can be generated through a computer-aided design (CAD) system; and/or any equivalent thereof. These 3D files are usually either ASCII or binary files that have a list of the triangular surfaces to describe the computer generated solid model. Depending on the material with which the 3D object is produced, the 3D object can be sanded, milled, drilled, tapped, painted, and/or electro-plated (e.g. nickel, gold, bright brass and antique brass, bronze and black chrome). Manual labor to clean, carve, and/or paint the 3D object into the final 3D object may be used to help assist in the final detailing of the object. Also, special printing systems and software may be used to produce the paper materials for the board games of the 3D objects. Since the technology involving fabrication of 3D objects is rapidly progressing, the applications and systems mentioned above are not meant as limitations to the implementation of this invention.

Another embodiment of this invention is providing the user the option to create a 2D/3D game 124 using their digital image files. The manufacturing center 123 will have the facilities to manufacture games using the latest 2D/3D game development system technology. Some examples of game design software include, but are not limited to the following: 3D GameStudio; GameSpace 3D; DarkBASIC Pro; GLBasic; 3D Adventure Studio; or any other game development system (i.e. game engine) that can develop the game models. These game development systems contain several components, such as 2D/3D engine, physics engine, terrain and texture editor, a library of 3D models, artwork, and programming languages. The user will select a storyboard and/or video game template from the available game storyboards and/or templates so that a manufacturing technician can incorporate the user's 3D image into the storyboard and/or template. Since the technology of producing games is moving forward rapidly, as with so many other facets of technology, the applications and systems mentioned above are not meant as limitations to the implementation of the present invention.

In another embodiment of this invention, the user also has the option to create an animated film 124 using their 3D digital image files. The manufacturing center 123, besides having 2D/3D game development systems, may also have digital content editing systems, such as the following: Avid system; Matrox Digisuite; Media 100; or any equivalent thereof. These systems can produce rich digital animation films for the user. The animation films are composed of background and texture images, plus the 3D images the user selected to be part of the animation film. During the shopping cart process 121, the user is presented with several storyboards which they can choose from to produce the animation films. The manufacture technician edits the content of the selected storyboard and adds the 3D images into the motion sequence of the film. When done editing the content, the technician submits the animation film to the QA group for evaluation. Since the technology related to producing films is progressing rapidly, the applications and systems mentioned above are not meant as limitations to the implementation of the system 100.

When the 3D model is produced, another QA process 125 is performed to verify and to determine whether the 3D model meets or exceeds the users' expectations. The manufacturing center 123 will have QA technicians that will follow specific steps to ensure that the model is manufactured to the highest level of quality for the user. If necessary, manual labor is performed to take care of the finer details of the 3D model before delivering it to the processing center 126. Also, in another embodiment, manufacturing center 123 generates a certificate (certificate of authenticity) to be sent with the 3D model. The certificate may have a unique certificate number which is tagged (e.g. engraved, labeled, or printed) onto the 3D model.

In another embodiment of the invention, after the manufacturing center 123 produces the 3D model, the processing center 126 verifies the 3D model to the original order and submits the purchase order information (e.g. user's name, address, model type) to the copyright system 127. The copyright system may prepare forms for signing and submission to the U.S. Copyright Office and/or any other foreign copyright office. When electronic filing and processing for copyright registration is available, the process of registering a copyright may be entirely automated. The processing center 126 applies a QA process to validate that the purchase order information does not correspond to a 3D model or 3D image that was previously filed and stored with the system. The QA process goes through several data validations, such as verifying the user name, verifying the 3D model type, verifying the date filed, and verifying any other information that will verify whether the particular 3D model or image corresponding to the user's purchase order information was already filed with the system. If the processing center 126 verifies that the 3D model or image has been previously filed with the system, the processing center will flag the image file, thereby notifying the user that the image and/or model has already been stored and filed with the system. If the processing center verifies that the image and/or model has not been previously filed with the system, the processing center generates a certificate of originality indicating that the image and/or model has not been entered into the system.

The 3D model and certificate of authenticity and/or certificate of originality are then transferred to a fulfillment center 128. When the model arrives at the fulfillment center 128, the 3D model undergoes the packaging and delivery process. The fulfillment center 128 is responsible for packaging the 3D model with the certificate(s) that states the model is authentic and/or original. The package is sent to the shipping address of the order or any other appropriate party if noted in the order form. Based on the 3D model type, different methods of packaging and delivery mechanisms can be used to help ensure the 3D model is not damaged in the delivery process. When the 3D model begins the delivery process, the order is updated to the system 100 databases 130 with notice of completion, and a notification (i.e. including but not limited to the order and tracking information of delivery agent) may be sent to the appropriate parties electronically (e.g. via email).

The user has the option in the system 100 to use an online auction store 114, 129 to sell his or her 3D model. The online auction store 129 will display available 3D model that has been defined by the user, using the user's own 3D image library via the digital lock box system 118. The system 100 is equipped with a complete set of tools to help manage the user's own private auction store 129. There are several options the user can choose. For example, the user may choose to sell 3D model that has already been manufactured and delivered. In this situation, the user would be responsible for packaging and shipping the models, since said model has previously been shipped from the fulfillment center 128 to the user. The system will send to the winner of the auction a new re-certification of the 3D model, access to the 3D image, and any historic data (i.e. unique tracking code that travels with the 3D image for purposes of authentication for the life span of the image). The previous owner of the 3D image will not have access to the image anymore.

Additionally, in another embodiment, the user may opt to sell 3D images from their own library 119, which would be manufactured once the winner of the auction is determined. This option will follow the same sequence of steps from the manufacturing center 123 to the fulfillment center 128 while shipping the 3D model with the certificate of authenticity under the name of the bidder that won the auction. The winner of the auction will then have access to the 3D image in their 3D image library, while removing the previous owner's access to the 3D image. The online auction store 129 may have many common auction features, including but not limited to the following: accepting bids; determining a winner; reserving pricing; minimum bids, start and end dates; bid increments; and/or private auctions. Also, it may have many of the e-commerce components commonly found in a web commerce server.

In the menu system 110, there is an option to manage the membership account 115 where the user can update and/or change the following information: membership account (e.g. first name, middle name, last name); billing information (e.g. card holder name, billing address, billing city, billing state, billing postal code/zip, billing country, credit card, expiration date, CVV2); shipping information (e.g. address, city, state, postal code/zip, country); email address; log-in (i.e. personal identification number, password) information; etc. Also, the user may view pending orders as well as any previous orders that were already processed in their account. Other menu options 116 may be added to the system 100, such as the following: frequently asked questions (i.e. to help educate the user on how to use the system 100); order tracking; or any other menu options that will help the user create their 3D models.

Figure 2A:
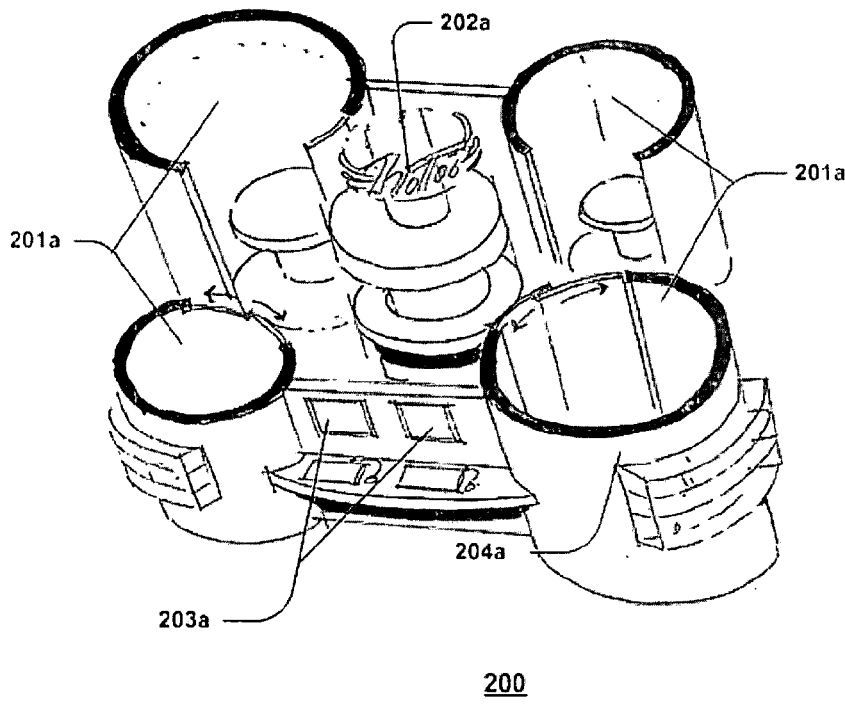
FIG. 2a is an overhead view of one embodiment of a retail store where users may purchase 3D models or create 3D images using 3D scanning cylinders, an embodiment of a 3D scanner.
Figure 2C:
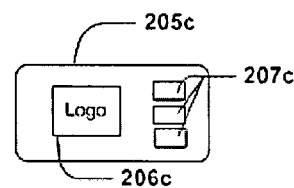
FIG. 2c is an illustration of one embodiment of a Body Scanning Image card.
Figure 2B:
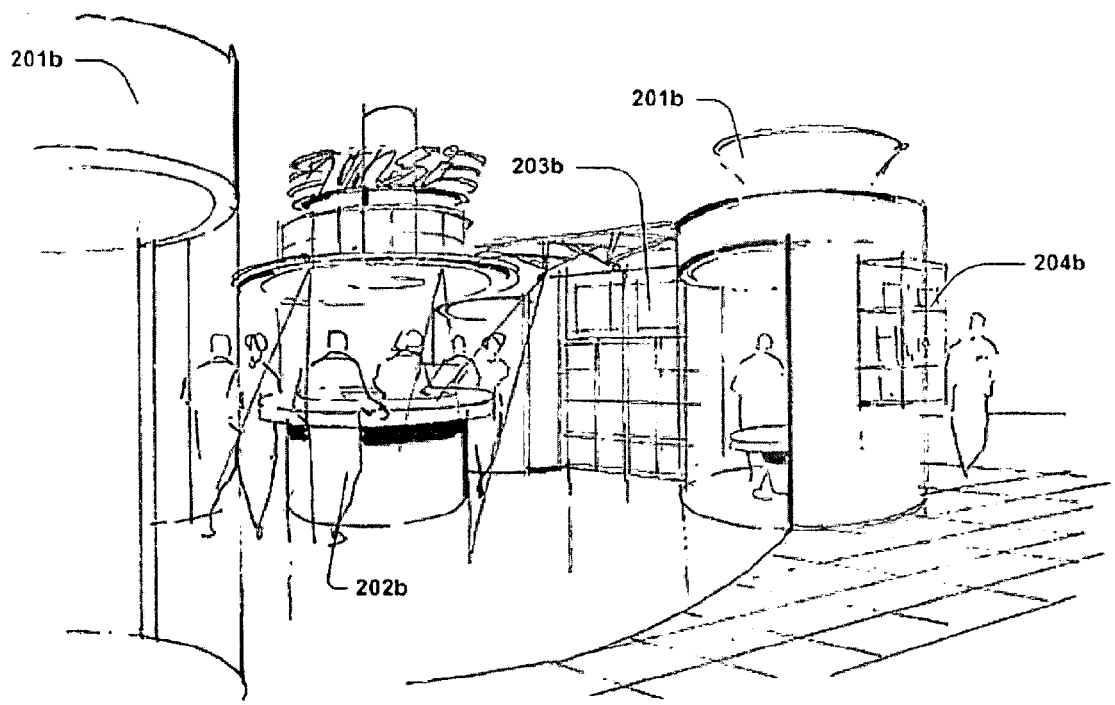
FIG. 2b is a first-person view of one embodiment of the retail store.

FIG. 2A and FIG. 2B both illustrate another embodiment of the invention in various angles. The retail store 102, 200 may serve as a vehicle to bring together the user (e.g. customer), artist, manufacturer, and designers in a digital retail environment that will allow them to exchange their creative ideas and products through the system 100. When the user goes to the retail store 102, 200 for body or model scanning, prior to any scanning, the user must have a membership account in the system 100. If it is a new user (e.g. customer), the user must register as a member in the system 100 via any of the computer workstations 203a, 203b at the retail store 102, 200. Each retail store 102, 200 will have a direct link via a network interface or via the Internet that has access to the system 100.

When the user is ready to create a 3D image, the user presents the membership number to the customer service technician and then the user enters the 3D image capturing cylinders 201a, 201b to create a digital 3D image which can be used to create 3D models. Also, the user may bring other models, including but not limited to the following: family members (group 3D objects); team members; pets that can stand still for required scanning time of the system (e.g. cats, dogs); or any other item to scan for creation of 3D models.

The 3D imaging cylinders 201a, 201b can be 3D color or black/white body or foot scanners that generate a 3D point cloud of the user or object. This 3D point cloud is composed of several million 3D points of data to assist in creating an accurate rendering of the 3D model. Since the scanning device 201a, 201b can record color texture, it provides a realistic 3D image of the user or object. The user or object is simply positioned in the center of the 3D imaging cylinder, within a circle which has been marked for ensuring equal measurements between the scanning columns 201a, 201b, while a laser source or any equivalent thereof (which cannot be harmful to the eyes) scans to collect the necessary data to create a 3D image.

When scanning is complete, the user can view the results of the 3D image on the computer monitors at the customer service stations 202a, 202b. When the user decides which 3D image to manufacture as 3D models, the user pays for the scanning service. Then, the retail store technician transfers the 3D image(s) into the user's system digital lock box 118 user account. The user has the option to place the order while being at the retail store 102, 200 using one of the computer workstations 203a, 203b to gain access to the system 100, or simply place the order at a later time. Samples 204a, 204b of 3D model types that users can have manufactured will be available for the user in the store.

FIG. 2C illustrates another embodiment of this invention where the user (e.g. customer) visits one of the stores 102, 200 and has the option of receiving a body scanning image (BSI) card 205c that records certain information about their body scanned image. While receiving the BSI card 205c, the user must enter a unique BSI PIN at a customer service station 202a, 202b in the retail store 102, 200 that would be used to secure card access. The card may record and contain information such as the following: the BSI PIN; user name; body-shape information (i.e. body measurements or sizes); membership information; and anything else a customer would need when they visit any third-party entity that has an agreement with the retail store 102, 200. This electronic card 205c may either have a magnetic storage medium and/or microprocessor chip that is compatible with magnetic card readers (i.e. credit card, debit card), smart card reader (i.e. smart card), or any other technology available to allow the storage of all necessary body shape information on the card. Also, this electronic card may have a logo 206c as well as advertisements 207c printed on it. Each third-party entity that has an agreement with the retail store 102, 200 may have a card reader device that interfaces with the system 100. When the user visits one of these third-party entities, they may swipe or insert the electronic card 205c (depending on the electronic card reader technology being used) at the customer service counter of the third-party entity and then enter their unique BSI PIN which authenticates the card user. If valid, the third-party entity system processes the card and prints a listing of recommended models (e.g. video games, garment size information) as well as discount coupons for the user, which they may redeem with their purchase. Also, at the card reader station, a monitor (e.g. LCD, plasma, TV) may display a 3D virtual dressing room with all the apparel pieces that is recommended using the customer's measurements. If the user enters the wrong BSI PIN value a specified number of times, the system 100 may lock the card access and the user must visit a retail store 102, 200 to reset the account. Also, this electronic card can be updated by visiting any retail store 102, 200 for a new body-shape image or to change other information stored on the card.

FIG. 3 illustrates one embodiment of the system 100 for locking and securing the 3D digital image files. The digital lock box system interface 118 is developed using any high-level programming language (e.g. C++, Java, VB.NET, C#.NET, Visual Basic) that produces an application programming interface (API)-compatible executable program. The API (e.g. COM, DLL, Web service) is a way for the digital lock box system 300 to communicate with other components in the system 100. The interface built-in logic 301 will process the request from the system 100 to add or retrieve 3D digital files. When a 3D image file is sent by the user to be added into their library (while inside the system 100 or via third-party entity 104), the validation engine 302 would process the file for, including but not limited to the following: file format (e.g. STL, PLY, VRML); file size; duplications; and anything else that would restrict the ability to manufacture 3D models. This QA process 303 will help eliminate problems with the digital file and protect the 3D images from copyright infringement. If the 3D image file passes validation, then it will be stored 303 in a storage device 131 with a unique key created from the lock box database 130. This unique key is then returned 303 and added to the user's 3D image library.

Any 3D digital file that does not pass the validation would return an unsuccessful confirmation via the interface 118.

As stated above, the retrieving logic 304 of the lock box system validates the submission of the key that was submitted by the user while inside the system 100. If the key does not exist, the validation process 304 returns an invalid confirmation to the user via the interface 118. If the key is already used, the copyright validation process 306 notifies the user. If the key refers to copyrighted models, the validation process 306 returns a copyright confirmation to the user via the interface 118. If the key is open (i.e. available to create models), then the key is processed 305 by changing the key's status (e.g. Copyright, Pending, Edit) in the database 130 and returns the 3D digital image file back to the user in the portal 109. Depending on which component inside the portal 109 is interfacing with the digital lock box system 300, the 3D image key status changes. For example, the interface from the 3D image engine 112 would change the 3D image key status to "Edit" while the interface from the shopping cart 121 would make the status "Pending."

In another embodiment, a first user may transfer access to the 3D digital image files stored in their digital lock box to a second user. For example, when a second user wins ownership of the first user's digital file via an online auction, a second unique digital key corresponding to the 3D digital file that was won in the online auction is created and provided to the second user. When the second user presents the second unique digital key to the first user's digital lock box system, the digital lock box system simultaneously enables the second user to access the 3D digital image file corresponding to the second unique digital key, while disabling the first user's first unique digital key from further access to the 3D digital image file.

Figure 4:
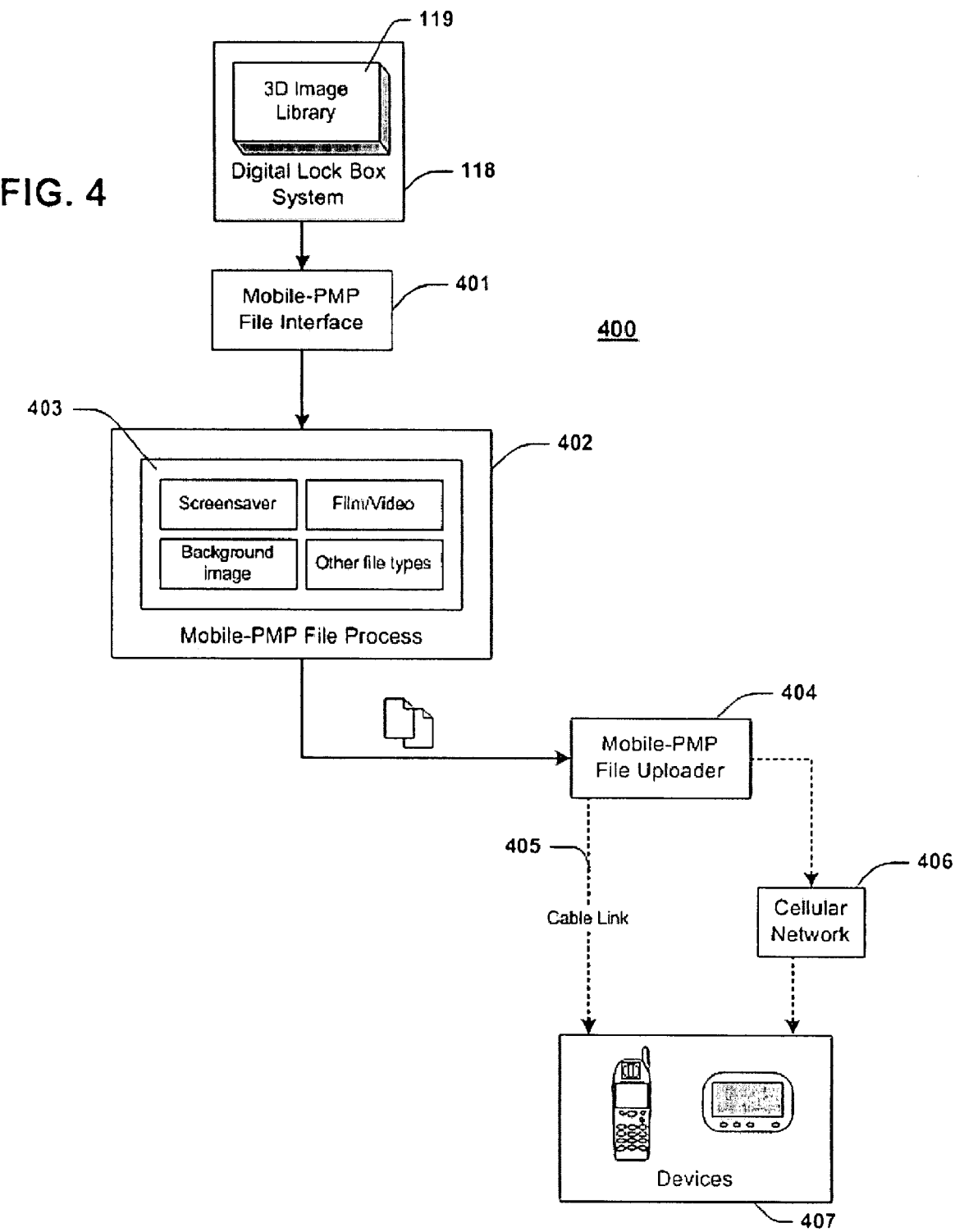
FIG. 4 is a flow diagram of one embodiment of a Mobile-PMP File Uploader system.

FIG. 4 illustrates another embodiment to this invention, providing the user the option to create an assortment of 3D products for their mobile and portable media player devices 407. These mobile and portable media player devices 407 must have sufficient display and audio capabilities to play different types of video and digital image formats, including but not limited to the following: mpeg; 3g2; Divx; Xvid; SigmaTel Motion Video (SMV); jpeg; gif; interactive media (i.e. flash animation); or any equivalent thereof. The mobile devices 407 should have at least some basic telephony functions, including but not limited to the following: a cellular phone 407; a wireless communication device (e.g. Blackberry, Treo, PocketPC, SmartPhone) 407, or any equivalent thereof. The invention may interface with several types of portable media player devices 407, including but not limited to the following: a PMP device 407; a media player device (e.g. iPod, Creative Zen, Archos, Iriver Clix) 407; or any equivalent thereof. These portable media player devices 407 may have wireless functionalities. The mobile and portable media player devices 407 can connect via a direct cable link (i.e. in any of the stores or third-party entity facilities) 405, Bluetooth connection, or any cellular network (e.g. W-CDMA, Third Generation (3G), GSM, PDC, FLEX, CDPD) 405 using some kind of wireless communication protocol (e.g. Wireless Application Protocol (WAP)) to download content files 403. These communication protocols must interface with several types of operating systems, including but not limited to the following: PalmOS; EPOC; Windows CE; FLEXOS; OS/9; JavaOS; in-house operating system; or any equivalent thereof. These cellular networks 406 can use either a "push" or "pull" technology to deliver content to the user's mobile and/or portable media player device 407 with or without user interaction. Some examples of 3D products the user can manufacture for their mobile and/or portable media player device 407 while using a 3D image in their 3D image library include, but are not limited to the following: 3D screensavers; 3D video; short clip-films; animated background image; or any equivalent thereof 403. Since the technology of mobile and portable media player devices 407 is moving forward rapidly, as with so many other facets of mobile and/or media content-making, the applications and/or systems mentioned above are not meant as limitations to the implementation of delivering content to mobile and portable media player devices 407.

When the manufacturing center 123 is ready to create the 3D product for either the mobile or portable media player device 407, the mobile-PMP file interface 401 retrieves the 3D image file from the users' 3D image library 119. Then, the manufacture technician evaluates the 3D image and applies the proper rendering process. Depending on the option the user picks for the type of 3D product for their mobile or portable media player device 407, different software solutions may be used. The mobile-PMP file process 402 applies several steps, including but not limited to the following: converting a 2D image into a 3D image; "texture mapping," "mapping," or "applying" to manipulate the 3D image geometry points into a series of frames to create an animated short-film; and/or any equivalent thereof. The manufacture technician may use any available software tool (e.g. 3D Max studio, Autodesk Maya, Cinema 4D), or any other tool that becomes available in the future to create the user's 3D content 403. When the manufacture technician has created the 3D product, the content file is transferred to the mobile-PMP file uploader 404. The mobile-PMP file uploader 404 is the service that will deliver the 3D product to the user's mobile or portable media player device 407. This service 404 may deliver the 3D product using a cable link 405, or using a cellular network 406. When the user places the order for their 3D product, he or she has the option to choose which delivery method to use. The cable link 405 method will always be available in the retail stores 102, 200 if the user changes his or her mind on how to receive their 3D product.

Figure 5:
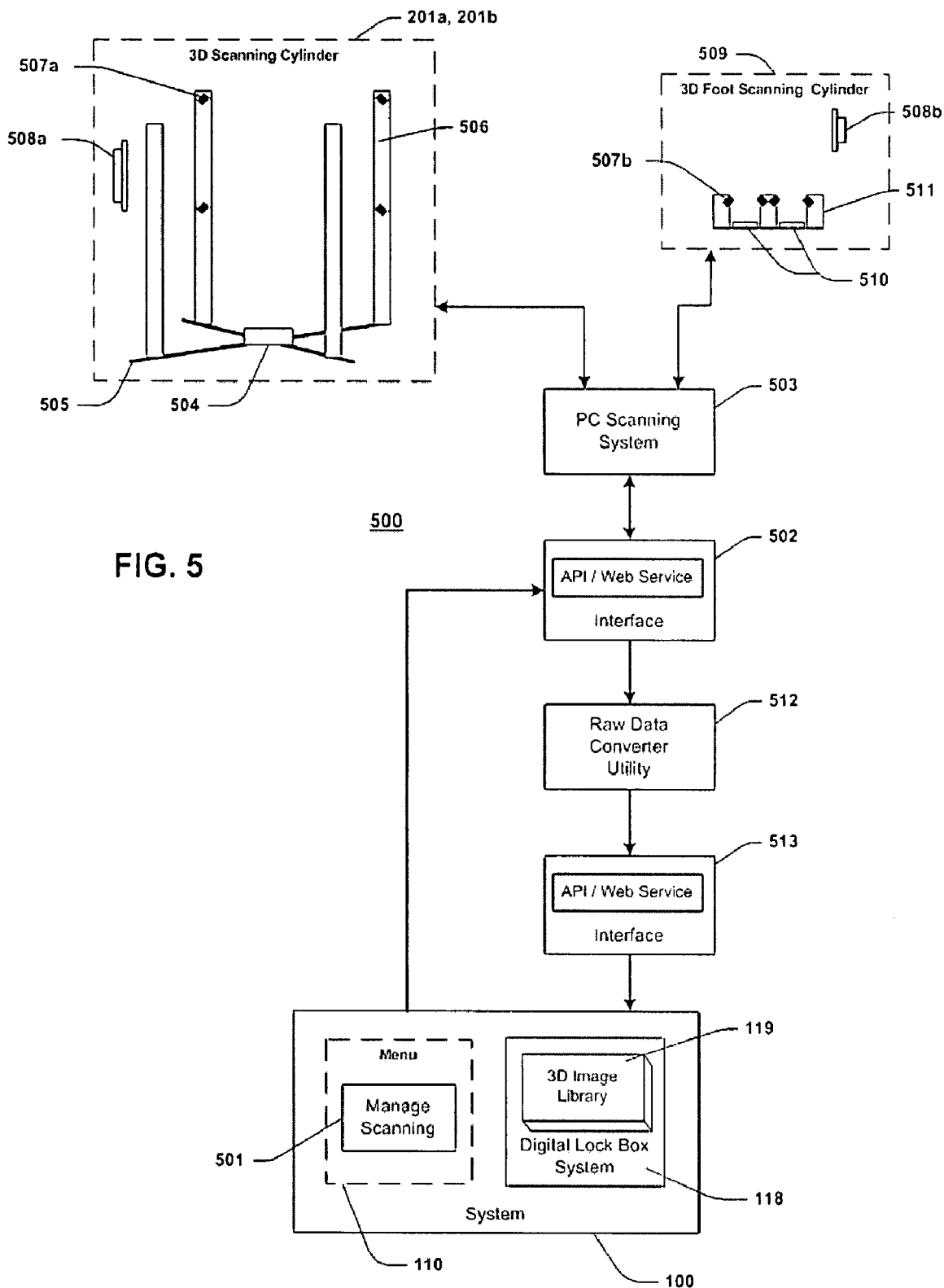
FIG. 5 is a flow diagram of the functionality of one embodiment of the 3D body and foot scanning cylinders.

FIG. 5 illustrates an embodiment of the interface between the system 100 and the 3D image capturing cylinder 201a, 201b, and 3D foot scanning cylinder 509. In one embodiment, when the user or object being scanned is standing on the platform 504, 510 inside the 3D imaging capturing cylinder 201a, 201b and 3D foot scanning cylinder 509, the customer service technician logs into the system 100 and goes to the managing scanning 501 feature to activate the scanning process. Inside this feature 501 the technician may swipe the customers BSI Card 205c if available or enter certain information, including but not limited to the following: user's membership number; number of scans; scan type (e.g. body, foot); and other specific information to store the 3D image file inside the user's 3D image library 119. The system 100 will communicate via an application interface or web service 502 and send several commands to the pc scan system 503. The first command will communicate with either the 3D imaging capturing cylinder 201a, 201b, or 3D foot scanning cylinder 509 and launch a video on the monitor (e.g. LCD, plasma, TV) 508a, 508b hanging adjacent to the outside of the scanning columns (e.g. pillars) 506, 511 area. This video may be a short-clip instruction film with relaxing music in the background, may be in several languages, illustrates to the user the proper scanning pose, and answers frequently asked questions. As the video ends, the second command triggers and launches a count-down video or audio informing the user of the time remaining before the 3D scanning system begins scanning. When the scanning device(s) 507a, 507b are finished scanning, they 507a, 507b generate a 3D point cloud of the user or object (e.g. body, foot) and transfer the raw data file to the pc scanning system 503. The pc scanning system 503 then "pushes" the new raw data file to the raw data converter utility 512 via an application interface or web service 502. The raw data converter utility 512 inputs the raw data file and applies a rendering process, including but not limited to the following: converting the raw data file into a CAD file format (e.g. STL, PLY, VRML); data compression; data cleaning; hole filling; and/or any equivalent thereof. The rendering process may output several files depending on the required file formats needed inside the system 100. The body scan data may be converted into a 3D model of the user or an "avatar." Another embodiment of the invention allows the user to use his/her 3D body model for the creation of customized apparel. This provides the option for the user to load their 3D body model in an interactive 3D virtual environment, such as a changing-room with apparel items from third-party entities 104. The user may apply various pieces of apparel and/or accessories on his/her avatar and view how it will look on him/her while also receiving apparel size information from the third-party entities 104. Aside from customized apparel, the user may manufacture their "avatar" as 3D models and upload their 3D model to any virtual world environments (e.g. Second Life®, There™, Kaneva, Active Worlds) and/or mobile or portable media player devices. Also, the user may use his/her 3D foot scan data to order customized shoes. Finally, the raw data converter utility 512 communicates via an application interface or web service 513 to the system 100 and uploads the new 3D file(s) inside the user's library 119.

The 3D imaging capturing cylinder 201a, 201b may be comprised of several configurations, depending on the detail level of the 3D image file required to be able to manufacture the 3D model. There are several 3D scanning technologies that may be used, including but not limited to the following: laser scanning; projection of white light patterns; active sensors; modeling and image processing; or any equivalent thereof. Several of the 3D scanning technologies use columns (e.g. pillars, metal poles) 506, ranging from two to four, to hold and/or house the scanning device 507a. The height of the columns 506 should be high enough to capture the tallest human being. These columns 506 may have a chain pulley device to help maneuver the scanning device 507a from top to bottom while scanning. Other 3D scanning technology may have extra non-moving scanning devices 507a to help capture the complete body or object. In another embodiment of this invention, these columns 506 may be attached to a metal base track 505 providing the flexibility to widen or reduce the scanning range for the scanning devices 507a. This feature provides the opportunity to zoom in closer to capture detailed head scans as well as scan larger objects or users. In the center of the columns 506, there is a platform 504 where the object or user stands to ensure that the proper scanning is captured correctly. Since the technology of 3D scanning is moving forward rapidly, as with so many other facets of body or object scanning, the applications and systems mentioned above are not meant as limitations to the implementation of the system 100.

Another embodiment to the invention is to have the 3D foot scanning cylinder 509 have the option to scan both feet at the same time. Also, it may have a single foot configuration depending on the detail level of a 3D foot image file required to be able to manufacture the 3D model. The 3D foot scanning system 509 may use the same 3D scanning technology that 3D imaging capturing cylinder 201a, 201b is using. The 3D foot scanning may use some kind of a rectangle box or columns to hold and/or house the scanning device 507b. This rectangle box or column 511 should be high and wide enough to capture the tallest human and/or largest foot. In the center of the rectangle box or column 511, there is a platform 510 where the user stands to ensure that the proper foot scanning is captured correctly. Since the technology of 3D scanning is moving forward rapidly, as with so many other facets of foot scanning, the applications and systems mentioned above are not meant as limitations to the implementation of the system 100.

Although details of specific implementations and embodiments are described above, such details are intended to satisfy statutory disclosure obligations rather than to limit the scope of the flowing claims. Thus, the invention is defined by the claims, not limited by the specific features described above. The invention is claimed in any form that falls within the proper scope of the appended claims, appropriately interpreted in accordance with the doctrine of equivalents.

What is claimed is:

1. A method of making, and distributing a three-dimensional model using a computer connected to a network, said computer having a machine readable storage, having stored thereon a computer program comprising a plurality of code sections executable by a machine, said method comprising the steps of:

receiving a digital image file via said network, said digital image file comprising data defining a three-dimensional model;

storing said digital image file in said machine readable storage;

accepting and storing purchase order information for said three-dimensional model;

receiving said purchase order information and said digital image file at a location wherein a three-dimensional object based on said three dimensional model and said purchase order information is manufactured; and delivering said three-dimensional object in accordance with said purchase order information.

2. A method of making, and distributing a three-dimensional model using a computer connected to a network, said computer having a machine readable storage, having stored thereon a computer program comprising a plurality of code sections executable by a machine, said method comprising the steps of:

receiving a digital image file via said network, said digital image file comprising data defining a three-dimensional model;

storing said digital image file in said machine readable storage;

accepting and storing purchase order information for said three-dimensional model;

receiving said purchase order information and said digital image file at a location wherein a two-dimensional or three-dimensional digital storyboard based on said three-dimensional model and said purchase order information is manufactured; and delivering said two-dimensional or three-dimensional digital storyboard in accordance with said purchase order information.

3. The method claimed in claim 2 wherein the step of manufacturing a two-dimensional or three-dimensional digital storyboard based on said digital image file and said processing order information further comprises the step of creating a digital storyboard using a video game development system.

4. The method claimed in claim 2 wherein the step of manufacturing a two-dimensional or three-dimensional digital storyboard based on said digital image file and said processing order information further comprises the step of creating a digital storyboard using a development system for creating digital animated films.

5. A method of making, and distributing a three-dimensional model using a computer connected to a network, said computer having a machine readable storage, having stored thereon a computer program comprising a plurality of code sections executable by a machine, said method comprising the steps of:
receiving a digital image file via said network, said digital image file comprising data defining a three-dimensional model;
storing said digital image file in said machine readable storage;
accepting and storing purchase order information for said three-dimensional model;
receiving said purchase order information and said digital image file at a location wherein a three-dimensional product, suitable for interaction with a mobile or portable media player device and based on said three-dimensional model and said purchase order information, is manufactured;
transferring said three-dimensional product to a mobile-PMP file uploader; and
delivering said three-dimensional product to said mobile or portable media player device.

6. A method of making, and distributing a three-dimensional model using a computer connected to a network, said computer having a machine readable storage, having stored thereon a computer program comprising a plurality of code sections executable by a machine, said method comprising the steps of:
receiving a digital image file via said network, said digital image file comprising data defining a three-dimensional model;
storing said digital image file in said machine readable storage;
accepting and storing purchase order information for said three-dimensional model;
processing said digital image file in accordance with said purchase order information;
creating a digital lock box, said digital lock box comprising a machine readable storage attached to said network, said digital lock box being electronically protected from public access through said network and being accessible through said network only upon presentation of at least a unique digital key;
creating a unique digital key to access said digital lock box and providing said digital key to a user authorized to access said digital lock box;
storing said digital image file in said digital lock box; and
transmitting a copy of said digital image file to said authorized user via said network upon presentation of said unique digital key.

7. The method claimed in claim 6, further comprising a method of transferring ownership to said three-dimensional model, said method further comprising:
displaying said digital image file from said digital lock box to third parties in an auction;
contacting the winner of said auction;
providing said winner access to said digital image file stored in said digital lock box;
and restricting previous owner of said digital image file from further access to said digital image file stored in said digital lock box.

8. A method of making, and distributing a three-dimensional model using a computer connected to a network, said computer having a machine readable storage, having stored thereon a computer program comprising a plurality of code sections executable by a machine, said method comprising the steps of:
scanning a three-dimensional person or object and obtaining scanning data generated through said scanning, said scanning data defining a three-dimensional model;
recording and formatting said scanning data to create a digital image file;
sending said digital image file to said machine readable storage;
storing said digital image file in said machine readable storage;
accepting and storing purchase order information for said three-dimensional model;
and processing said digital image file in accordance with said purchase order information.

9. The method claimed in claim 8 wherein the step of recording said data further comprises storing said scanning data on an electronic card.

10. The method claimed in claim 8 wherein said scanning data is uploaded into an interactive three-dimensional, virtual environment.

11. A method of making, and distributing a three-dimensional model using a computer connected to a network, said computer having a machine readable storage, having stored thereon a computer program comprising a plurality of code sections executable by a machine, said method comprising the steps of:
creating a three-dimensional digital image file by modifying a pre-existing digital image file in accordance with predetermined geometry and texture information, said pre-existing digital image file comprising data defining a two dimensional digital image or a three dimensional digital image;
sending said three-dimensional digital image file to said machine readable storage;
storing said digital image file in said machine readable storage;
accepting and storing purchase order information for said three-dimensional model;
and processing said digital image file in accordance with said purchase order information.

* * * * *